United States Patent
Kline

(10) Patent No.: US 8,426,328 B2
(45) Date of Patent: Apr. 23, 2013

(54) SURFACE-ETCHED ETCHED ALUMINA/SIC MINI-WHISKER COMPOSITE MATERIAL AND USES THEREOF

(75) Inventor: C. Robert Kline, Austin, TX (US)

(73) Assignee: C. Robert Kline, Austin, TX (US)

( * ) Notice: Subject to any disclaimer, the term of this patent is extended or adjusted under 35 U.S.C. 154(b) by 0 days.

(21) Appl. No.: 13/395,843

(22) PCT Filed: Sep. 24, 2010

(86) PCT No.: PCT/US2010/050167
§ 371 (c)(1),
(2), (4) Date: Mar. 13, 2012

(87) PCT Pub. No.: WO2011/038206
PCT Pub. Date: Mar. 31, 2011

(65) Prior Publication Data
US 2012/0172474 A1    Jul. 5, 2012

Related U.S. Application Data

(60) Provisional application No. 61/245,600, filed on Sep. 24, 2009.

(51) Int. Cl.
*C04B 35/00* (2006.01)
*C08K 3/18* (2006.01)
*A61F 13/15* (2006.01)

(52) U.S. Cl.
USPC ............ 501/95.3; 501/89; 523/218; 524/430; 521/149

(58) Field of Classification Search .................. 521/149, 521/170; 501/89, 95.3; 524/430; 523/218
See application file for complete search history.

(56) References Cited

U.S. PATENT DOCUMENTS

| | | | | |
|---|---|---|---|---|
| 4,391,924 A | * | 7/1983 | Uram, Jr. ..................... | 523/466 |
| 4,595,453 A | * | 6/1986 | Yamazaki et al. ............ | 438/718 |
| 4,673,658 A | * | 6/1987 | Gadkaree et al. ............. | 501/89 |
| 4,740,395 A | * | 4/1988 | Tsunekawa et al. .......... | 427/455 |
| 5,209,819 A | * | 5/1993 | Suzuki et al. .................. | 216/23 |
| 5,480,676 A | * | 1/1996 | Sonuparlak et al. .......... | 427/180 |
| 5,730,792 A | * | 3/1998 | Camilletti et al. ....... | 106/287.14 |
| 5,780,163 A | * | 7/1998 | Camilletti et al. ............ | 428/446 |
| 6,826,996 B2 | * | 12/2004 | Strait .......................... | 89/36.02 |

(Continued)

FOREIGN PATENT DOCUMENTS

| | | |
|---|---|---|
| CN | 1357583 | 7/2002 |
| JP | 63-030377 | 2/1988 |
| WO | WO 99/28690 | 6/1999 |
| WO | WO 2005/047025 | 5/2005 |

OTHER PUBLICATIONS

International Search Report and Written Opinion for corresponding International Patent Application No. PCT/US2010/050167 mailed Jun. 23, 2011.

*Primary Examiner* — Hannah Pak
(74) *Attorney, Agent, or Firm* — Swanson & Bratschun LLC

(57) ABSTRACT

A composition of matter comprising 0.01 to 35% by weight of $Al_2O_3$, having a length of 10-20 μm and a surface altered by wet etching, 0.01 to 98% by weight of SiC, having a length of 10-20 μm and a surface altered by dry etching; and 0.01-15% by weight of kaolin, altered by treatment with $Na_2SiF_6$, with the above constituents being blended into a $SiC/Al_2O_3$ composite. Alternative embodiments are methods of producing the compositions described above. Further embodiments include products made by the process described above.

21 Claims, 1 Drawing Sheet

U.S. PATENT DOCUMENTS

2005/0276961 A1* 12/2005 Sherwood et al. ......... 428/292.1
2008/0139709 A1* 6/2008 Piccirilli et al. ................ 524/99
2008/0160464 A1* 7/2008 Ghani et al. ...................... 431/9
2008/0241516 A1* 10/2008 Hong et al. ................... 428/331

* cited by examiner

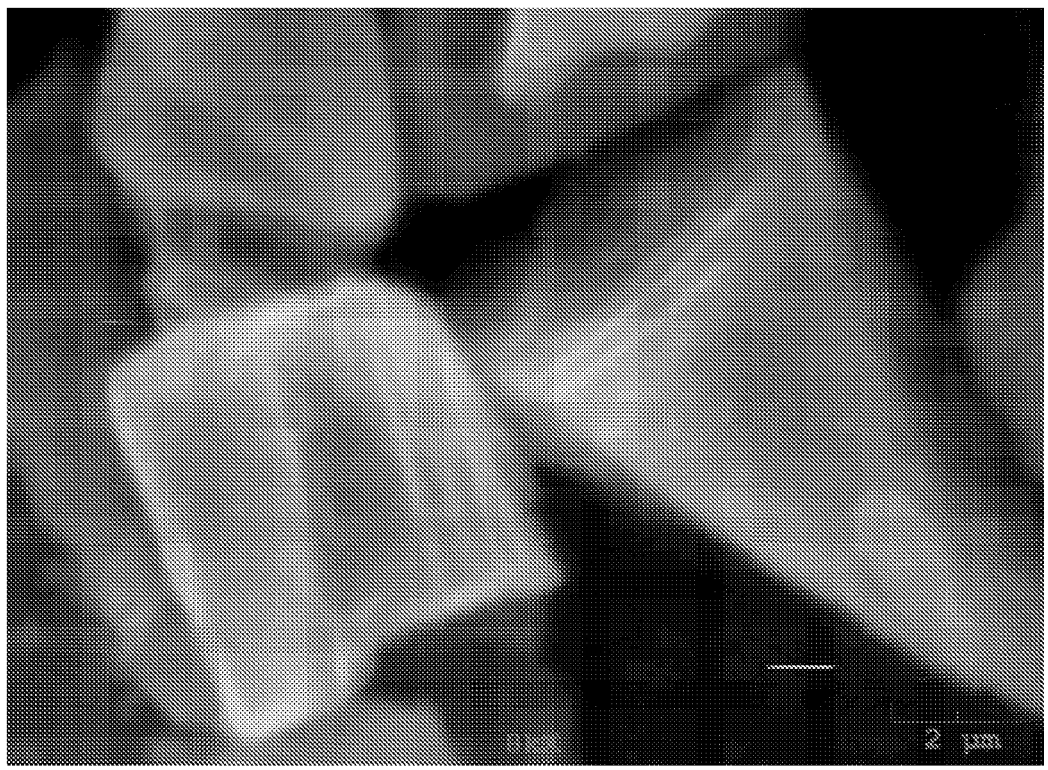

SURFACE-ETCHED ETCHED ALUMINA/SIC MINI-WHISKER COMPOSITE MATERIAL AND USES THEREOF

RELATED APPLICATIONS

This application is a 35 U.S.C. §371 national phase application of PCT/US2010/050167 (WO 2011/038206), filed on Sep. 24, 2010, entitled "Surface-Etched Etched Alumina/SiC Mini-Whisker Composite Material and Uses Thereof", which application claims the benefit of U.S. Provisional Application Ser. No. 61/245,600, filed Sep. 24, 2009, which is incorporated herein by reference in its entirety.

BACKGROUND

Silicon carbide (SiC), also known as carborundum, is a compound of silicon and carbon with chemical formula SiC. SiC may be produced in many forms, including but not limited to bulk ceramic materials, grains and filaments. Bulk or granular SiC has numerous uses including use as abrasive or cutting tools, a structural ceramic, in electronic circuit components and heating elements. SiC can also be produced in a whisker form. As is customary in the SiC production industry a "whisker" is defined as a SiC particle having a high aspect ratio of length to diameter. SiC whiskers of various sizes and manufactured by various techniques are often used to reinforce or toughen other materials.

The earliest SiC whiskers produced were fabricated from rice hulks (husks) and intense pressure in a $SiO_2$ atmosphere. Later SiC whiskers were produced using petrochemical processes, and most recently production has relied on direct fluorination at high temperatures. A promising approach uses a $SiO_2$—$CH_4$—$Na_3AlF_6$ process, for example. Some attention has recently been focused on formation of molybdenum silicide-SiC powders produced in a similar manner.

Thus, known processes use either: (i) very high temperature for reacting constituents into the desired SiC, (ii) expensive and difficult to handle petrochemical derivatives (such as benzoxazine, toluene) or (iii) expensive precursors (e.g., $B_4C$, "boron carbide"). For example, typical known processes occur at greater than 1,000° C., up to 2,200° C. which becomes problematic because higher temperatures demand different furnaces/processes with more critical control-related problems, for example, feed speed, time controlling in heat zone, gas discharge, heat discharge, and power quality monitoring.

The embodiments disclosed herein are directed toward overcoming one or more of the problems discussed above.

SUMMARY OF THE EMBODIMENTS

One embodiment disclosed herein is a composition of matter, in particular a surface-etched etched alumina and SiC mini-whisker composite material. The composition of matter comprises at least three constituents; 0.01 to 35% by weight of $Al_2O_3$, having a length of 10-20 μm and a surface altered by wet etching, 0.01 to 98% by weight of SiC, having a length of 10-20 μm and a surface altered by dry etching; and 0.01-15% by weight of kaolin, altered by treatment with $Na_2SiF_6$, with the above constituents being blended into a $SiC/Al_2O_3$ composite. The $Al_2O_3$ surface may be wet etched with buffered hydrofluoric acid. The SiC surface may be dry etched with tetrafluoroethylene or polytetrafluoroethylene. In addition, the composition may include SiC and $Al_2O_3$ each in the β form. In certain embodiments the kaolin component of the composition will be comprised of 99.99% or greater purity kaolin. The ratio of constituent materials of the composition described above may be varied as desired to achieve selected mechanical or physical properties.

Alternative embodiments are methods of producing the compositions described above. The method includes providing $Al_2O_3$ having a length of 10-20 μm and a surface altered by wet etching; providing dry kaolin blended with $Na_2SiF_6$; providing an additional fluorination material and providing SiC, having a length of 10-20 μm. The method further includes blending together 0.01 to 35% by weight of $Al_2O_3$ into 0.01 to 98% by weight of SiC along with the fluorination material and the prepared kaolin. The kaolin blended with $Na_2SiF_6$ provides a combination fluorinating material, blending agent, and a source of lower temperature direct fluorination. the method further includes heating the blend of $Al_2O_3$, SiC, kaolin and the fluorination material.

The method of producing the composition described above may include using a high speed gas dryer to remove up to 99% of the water from the blended mixture. The mixture may be processed at temperature range of 800-810° C. Processing may occur in a device such as a fluid bed dryer, a conveyor oven, a rotary kiln, a calciner, a ceramics furnace or similar device. The method may also include adding the resulting composition to another material to form a product.

Accordingly, further embodiments disclosed herein include products made by the process described above. The product may simply be $Al_2O_3$/SiC composition of matter. Alternatively, the $Al_2O_3$/SiC composition may be formed into a subsequent product by adding the $Al_2O_3$/SiC composition to another material. Products formed by this method include but are not limited to syntactic foam, an electronic device, an electromechanical device, a coating, a ceramic composite product, a composite bearing, a mechanical device, a medical device or an article fabricated from HNBR rubber, cast polyurethane, a vinyl ester or a thermoplastic urethane including the $Al_2O_3$/SiC composition as an additive.

BRIEF DESCRIPTION OF THE DRAWINGS

FIG. 1 is an electron microscope image of an $Al_2O_3$/SiC composition consistent with the embodiments disclosed herein.

DETAILED DESCRIPTION

Unless otherwise indicated, all numbers expressing quantities of ingredients, dimensions reaction conditions and so forth used in the specification and claims are to be understood as being modified in all instances by the term "about".

In this application and the claims, the use of the singular includes the plural unless specifically stated otherwise. In addition, use of "or" means "and/or" unless stated otherwise. Moreover, the use of the term "including", as well as other forms, such as "includes" and "included", is not limiting. Also, terms such as "element" or "component" encompass both elements and components comprising one unit and elements and components that comprise more than one unit unless specifically stated otherwise.

I. Alumina/SiC Mini-Whisker Composite Composition of Matter.

One embodiment disclosed herein is a composition of matter, in particular, a surface-etched etched alumina and SiC mini-whisker composite material. The embodiments include but are not limited to a composition of surface-etched alumina and/or surface-etched SiC, of less than 250 μm in longest aspect, and more particularly a composition of surface-etched alumina and/or surface-etched SiC, of equal to or less than 25

μm in longest aspect, in a ceramic matrix composite (CMC), said particles being etched by a buffered hydrogen fluoride solution (BHF) and treated with other chemical processes, resulting in etched alumina and/or etched SiC mini-whiskers. The whiskers have many uses including certain selected uses as described in detail below, for example in syntactic foam characterized as having the density of sea water at 10-35° C.

The compositions disclosed herein may be characterized as being a composite of:

(i) 0.01-35% by weight of 10-20 μm Alumina ($Al_2O_3$), altered by wet a etching process including, but not limited to reactive ion etching (RIE), (ii) 0.01-98% by weight of 10-20 μm SiC, altered by dry etching in tetrafluoroethylene or polytetrafluoroethylene ($C_2F_4$ or $C_2F_{4x}$), and (iii) 0.01-15% by weight of substantially pure (i.e. 99% pure) kaolin, altered by treatment with Sodium Fluorosilicate ($Na_2SiF_6$), the above constituents being blended into a SiC/$Al_2O_3$ composite.

The compositions described herein comprise certain constituents and have a resulting morphology which is different from known compounds. For example, embodiments of the composition include SiC and a combination of:

(i) kaolin treated with Sodium Fluorosilicate, $Na_2SiF_6$
Sodium Fluorosilicate is a low cost crystalline white powder commonly used in fluorinating municipal water supplies. The kaolin treated with Sodium Fluorosilicate is used in combination with pre-wet-etched $Al_2O_3$ (described immediately below) as a blending agent as well as a source of fluorine for direct fluorination of the SiC.

(ii) pre-wet-etched $Al_2O_3$ which is used as a blending and wetting agent which disperses rapidly. The pre-wet-etched $Al_2O_3$ and kaolin treated with $Na_2SiF_6$ together with a direct fluorination material create an "activation material" for the reaction which creates the composite. In particular, the enriched kaolin ensures complete breakdown and dispersion of any subsequently used direct fluorination material, for example polytetrafluoroethylene (PTFE) or tetrafluoroethylene (TFE). During manufacture, the direct fluorination of the SiC is thus begun by the $Na_2SiF_6$ which enables a low cost manufacturing process. In addition, the pre-etched $Al_2O_3$ adds structural and thermal qualities to the resulting composite and also independently ensures complete breakdown and dispersion of the fluorinating material.

(iii) a fluorinating material, for example PTFE or TFE.

The resulting compositions may be described as "mini whiskers" and are a combination of $Al_2O_3$ and SiC which have both been etched into a β-SiC composite or, in some proportions a β-SiC/$Al_2O_3$ composite.

The compositions disclosed herein have some of the same qualities of mullite whiskers and β-SiAlONS but retain the mechanical and thermal properties of SiC and $Al_2O_3$ as is useful in specific applications. For example, the disclosed compositions may be incorporated into the epoxy/microsphere matrix of syntactic foam, without significantly altering the specific density of the foam or its other special properties while enhancing desirable mechanical and thermal properties.

It is important to note that the compositions of matter disclosed herein include a range of constituent component ratios, as is described in more detail in section III below and in Table 1. It has been determined that compositions having selected constituent ratios perform more effectively for certain specific uses.

The disclosed compositions may be distinguished from known SiC mini-whiskers and typical etched alumina in several ways. The disclosed composition always includes kaolin and $Al_2O_3$ in combination with SiC, in addition, the methods of production are significantly different as described below. Combining SiC and alumina has been found to produce materials having advantageous properties. For example, "Thermal shock testing of an alumina-20 vol % SiC whisker composite showed no decrease in flexural strength with temperature differences up to 900° C. Alumina, on the other hand, normally shows a significant decrease in flexural strength with a temperature change of >400° C. The improvement in the thermal shock resistance of the composite is believed attributable to the increased fracture toughness of this material. Tiegs, T. N. and Becher, P. F. *Thermal Shock Behavior of an Alumina-SiC Whisker Composite*, Journal of the American Ceramic Society. 70 (5): C-109-C-111 (May 1987).

The reason for the enhanced thermal shock resistance of an alumina/SiC composite is possibly related to the transgranular fracture mode. In particular, known "Alumina/SiC "nanocomposites" consist of a dispersion of SiC "nanoparticles" in an alumina matrix with conventional grain size. The nanocomposites are much more resistant to severe wear than pure alumina. . . . The results show that the reduction in wear rate caused by the SiC is a consequence of the reduction in surface pullout by brittle fracture only. For small volume fractions (5 vol %), the main effect of the SiC additions is to reduce the dimensions (diameter, depth) of the individual pullouts. This is suggested to be a consequence of the change in fracture mode from intergranular in alumina to transgranular in the nanocomposites. For greater additions of SiC nanoparticles (10 vol %), the brittle fracture responsible for the cracking is also suppressed, and it is proposed that this is a consequence of the blocking of the formation of the long twins or dislocation pileups that are thought to be responsible for crack initiation by intragranular SiC particles (i.e. a form of slip homogenisation). "[Todd, R. I. and Limlichaipanit, A. *Microstructure-Property Relationships in Wear Resistant Alumina/SiC Nanocomposites*," Advances in Science and Technology (45, 2006): 555-563.

FIG. 1 is an electron microscope image of the recited composition. In particular, a view of the etched edges of the material is shown. As illustrated, the whiskers are deeply etched with parallel etches but the whiskers are not uniform in shape. For this reason the composition blends well into various matrices.

II. Method of Production of Surface-Etched Alumina and Surface-Etched SiC Mini-Whisker Composite Materials.

Methods of preparing the compositions described above include the use of buffered hydrofluoric acid (BHF) pre-wetted alumina. The BHF pre-wetted alumina may be blended directly into fluorine-etched SiC using dry kaolin blended with $Na_2SiF_6$ as a combination fluorinating material, blending agent, and source of lower temperature direct fluorination. A supplemental or additional direct fluorinating agent such as PTFE or TFE may be added prior to activation as well.

The methods of preparation may alternatively include using high speed gas drying to remove about 99% of the water from any mixture. The methods of preparation will also typically include processing the mixture at 800-810° C. The method of preparation may selectively involve using processing apparatus including but not limited to a fluid bed dryer, conveyor oven, rotary kiln, calciner, or ceramics furnace as the principle heated processing device. Specific preparation methods are detailed below.

The disclosed compositions and production methods feature several advancements over known compositions and methods. The benefits of the disclosed embodiments include, but are not limited to the following: (1) processing times are relatively short, enabling large quantity production on a continuous basis at relatively low cost; (2) the material produced combines easily and uniformly into other substances, for example a microsphere filled syntactic foam.

The rapid production of the disclosed compositions is made possible by the use of a pretreated activation material. Generally, the activation material comprises pre-wet-etched $Al_2O_3$ and kaolin treated with $Na_2SiF_6$ and a direct fluorination material. The activation materials may be rapidly mixed with the SiC, and treaded quickly with high heat in a concentrated Nitrogen-Air-HF atmosphere. In particular, heating kaolinite $(Al_2Si_2O_5(OH)_4)$ from ambient to approximately 750° C. creates metakaolin $(2Al_2Si_2O_7+4H_2O)$, as a result o endothermic breakdown which begins at about 600° C., a stage which is on the way to the material becoming gamma-alumina $(Si_3Al_4O_{12}+SiO_2)$. This process, used to create β-SiAlONS, is used in the generation of mullite whiskers for example.

Combining the activation materials (kaolin, BHF-treated $Al_2O_3$, and, for example, PTFE or TFE) with the dry SiC creates randomly diverse length orthorhombic β-SiAlONS-like "whiskers" of SiC. It is these characteristics which lead to the enhanced thermal and mechanical performance of various materials produced with the composition, for example, syntactic foam deployed at great subsea depths. Similar characteristics, especially the randomly diverse lengths, provide enhanced mechanical properties in materials or products, for example syntactic foam-filled armor, blast shielding materials and other materials—due principally to the "settling" of the diverse lengths in random combinations.

The disclosed methods can be implemented at temperatures which are relatively lower than typical SiC fabrication temperatures because $Na_2SiF_6$ begins to outgas at 500° C., which is the rise temperature of selected embodiments disclosed herein. This early gassing process begins the etching of the SiC much earlier than other known processes. This in turn increases speed of production and decreases the quantity of exhaust gas, specifically HF, to be handled. In turn, this results in reduced scrubber and treatment water equipment costs.

One representative process consistent with the disclosed embodiments is as follows:
$Al_2O_3$ is wet etched with BHF in a microelectronics etch basin, creating angularly etched orthorhombic structures evidencing reduced oxide layering;
Kaolinite/kaolin is blended by compression with $Na_2SiF_6$;
The wet etched $Al_2O_3$ is blended uniformly with the enhanced kaolinite/kaolin at a selected ratio; and
This blended/wetting agent-treated material is reserved.
The dry etch material (tetrafluoroethylene or polytetrafluoroethylene ($C_2F_4$ or $C_2F_{4x}$)) is added to the reserved blending/wetting agent at a specified ratio and mixed steadily. When the dry etch material is fully added the mixing continues for a specified amount of time to ensure the resulting uniformly blended material is in as uniform condition as possible.
SiC is added into this blended etched $Al_2O_3$, enhanced kaolin, and dry etch material in a selected amount, while mixing continues. The resulting etching is easily seen in FIG. 1.
This stock is heated to approximately 805-810° C.
The now-uniform mini β-SiC/$Al_2O_3$ whiskers are cooled.
In various use described below embodiments, the produced material is added into another material, product or structure, for example, syntactic foam.

The scope of the disclosure includes both the recited methods and compositions or products made by the recited methods.

The methods described above may be distinguished from known Sic or alumina whisker preparation methods. For example, known production methods would include mixing PTFE with SiC or with $Al_2O_3$ followed by heating of the mixture to cause the PTFE to flash-over into HF which in turn causes the HF to etch the material. The disclosed methods are substantially different in at least three ways:
The use of kaolin to help break up the PTFE or other fluorination additive and keep it from clumping;
The use of BHF alumina as both an abrasive agent during the mixing steps and a constituent material for production;
The inclusion of both alumina and SiC in the material—with both processed to the point of being a β material.

The resulting β material compositions blend better, are stronger, have advantageous thermal conduction characteristics and, because of the recited production techniques are more homogenous than other products made with other methods.

The disclosed methods provide distinct production advantages including but not limited to:
More complete breaking down of the fluorinating agent, for example PTFE, and more complete blending into the materials to be etched sets up both a faster production and a more homogenously blended/distributed product. More rapid production results in lower cost; more homogenous compositions result in a product that is easier to use with other materials, such as carbon black and syntactic foams;
The faster rise time to catalysis results in a shorter dwell time in the processing chamber, resulting in lower expenses of production;
The faster rise time results in more etching gas on the material surfaces for a longer period. Thus, with the faster rise time more useful etching gas is generated more quickly and less undesirable outgassing occurs. In particular, the toxicity of gas produced from heating PTFE is at a maximum as the heat rises from about 350 to 500° C. At temperatures higher than 650° C., the primary gasses produced are carbon dioxide and carbon tetrafluoroide. It is the temperature range between 350 and 500 C.° which must be quickly passed through for maximum safety. The undesirable gassing between 350 and 500 C.° includes a powerful chemical warfare agent (PFIB) and TFE (among other undesirable fumes). The scrubbing of these undesired gasses dramatically adds to production costs, which due to safety concerns cannot be reduced significantly. The disclosed methods provide the producer with means to "jump" over this toxic heat zone, primarily by the inclusion of the BHF and prewetted materials which dramatically shortens the initial heating phase, reducing it by over half to 10 seconds or less, from 25-28 seconds as the material moves through the furnace/calciner/oven processing system.
The phenonema described above also directly result in the use of less PTFE per given production volume than earlier methods. PTFE is the most expensive material in the production process for either etched SiC or etched alumina. Thus, the disclosed compositions can be produced at costs comparable to the production of standalone SiC or alumina.

III. Use of Surface-Etched Alumina/Surface-Etched SiC Whiskers in Various Applications.

The compositions prepared as above may be used in various and diverse practical implementations. All uses of the compositions prepared as above are within the scope of this disclosure. Selected uses are described in detail below. The scope of this disclosure is not intended to be limited to the particular uses described below in detail.

A. Providing Thermal and Mechanical Enhancements to Enhanced Syntactic Foam, Whether Made with Polyurethane, Polypropylene or Epoxy Resins, for Deep Subsea Use.

One method of use of the compositions prepared as described above includes adding the etched alumina/SiC mini-whisker composite material at 7.5-15%/wt. to a mix of microspheres and syntactic foam base resin for use in the preparation of syntactic foam for the deep subsea insulation of risers, feed pipes and crucial metal parts used in the oil, gas or mineral extraction industries.

Subsea, and especially deep subsea, syntactic foam is an epoxy, polyurethane, or polypropylene material into which microspheres of one or more sizes are added. Microspheres are typically recovered from the fly ash byproducts of coal fired electric power plants and are very light weight even though the microspheres contain significant amounts of calcium, silica, alumina, and iron. Alternatively, microspheres can be produced using thermoplastic polymers but this production is more expensive than taking fly ash out of waste stream scrubbers. Recently, the use of manufactured glass microspheres has been capturing increasingly large numbers of applications. The combination of a foam precursor material with the microspheres and in turn the addition of the etched alumina/SiC composite mini-whiskers disclosed herein provides mechanical and thermal enhancement of the finished coating. As flow line lengths continue to increase these thermal and mechanical properties become more important. For example, flow lines over 40 km [25 mi] which were once considered long are now common. Similarly, the increased depths of drilling (commonly 1.6 to 3.2 km or 1 to 2 mi) requires increased attention to insulation having enhanced thermal and mechanical operating ranges.

Specific mechanical enhancements afforded syntactic foam prepared as described herein includes enhanced "bend-flex" characteristics, improved resistance to colliding particles and/or shock mitigation, and resistance to penetration by sea water. In addition, a syntactic foam prepared with the etched alumina/SiC composite mini-whisker compositions extends the thermal range of use of the syntactic foam significantly, from 170° F. to 360° F., based on major deep subsea HAST tests performed in deep subsea environments. While syntactic foams have lifetimes measured in decades, 2 to 2½ decades are common requirements, the blended syntactic foams disclosed herein exhibit equivalent or longer life while offering enhanced thermal and mechanical protection.

B. Providing Advantages in Armor Implementations and Other Defense Applications.

Another use of the disclosed materials includes employing the compositions as a lightweight strengthening or reinforcing material added to syntactic foam used with armor. For example, the composite material may be encapsulated within rigid barriers, spaced evenly between 0.25-1.5" in a honeycomb, or between two armor plates, for use in defense or other applications requiring lightweight strong armor. The resulting armor multi-laminate may have an areal density of less than 18 pounds/square foot and still maintain superior defensive characteristics. Furthermore, the disclosed etched alumina/SiC composite mini-whiskers or variations thereof provide enhanced mechanical properties in armor and blast-shielding plates, especially for increased energy absorbing resistance with dampening of high heat energy pulses.

The mechanism of increased shock and ballistic resistance is based in an extension of the generally known structural "Theory of Constraint," whereby a constrained material will absorb shock based on its local environment, for example a small "cell" and then release the incident shock pulse into the next adjoining cells. If, therefore, there were a 3×3 matrix of cells and shock were to be directed at the center 2×2 square the smaller 2×2 unit would "take the shock" and then release into the outer 3×3 layer. The incident sock would have been mitigated by its impact with the inner smaller grouping and the travel of the shock pulse and attenuation that 2×2 group of cells provided. If the 3×3 grouping were to be surrounded by another layer or more than one layer, then the attenuation would continue, but not in a linear fashion since a drop in shock load/pressure would occur in each layer, further reducing the shock pulse pressure into the next grouping.

By using this principle with layers and very small cells, a honeycomb with both latitudinal and vertical layering is possible. The light weight and enhance strength of a foam prepared with the disclosed compositions enhances the performance of armor plate on either side without greatly increasing the weight of the composite armor unit. This results in a dramatic performance and weight improvement over ceramic armor or regular rolled homogenous armor (RHA) plate.

C. Providing Thermal and Mechanical Enhancements to Carbon Black

Production carbon black is an amorphous, high surface-area-to-volume ratio carbon material used principally in tire production as a pigment and as a strengthener/reinforcing material. Carbon black also helps to provide desirable thermal conduction properties within the tire rubber. The enhanced whisker compositions disclosed herein have been proven efficacious as a reinforcement and hardener for various rubber materials. Adding the disclosed materials to production carbon black results in additional strengthening of the carbon black within the tire rubber. Notably, the thermal enhancements provided by carbon black in tires are not noticeably compromised by the addition of the lower thermal conductivity composite whiskers.

Tests indicate that a blend ratio of 1.75% to 2.5% alumina/SiC whiskers carbon black, by weight, provides substantial enhancement of mechanical characteristics with no degradation in thermal conductivity. Lower ratios, for example less than 1.70% of the alumina/SiC composition provide less mechanical improvement; ratios over 2.5% by weight prove to result in no additional mechanical improvement and a blend ratio of above 3.25% alumina/SiC composition shows the beginning of reduction in desired thermal conductivity levels. Baseline reinforcement improvements are shown to be 15-18% greater strength. Since the ratio of alumina/SiC whiskers to carbon black is generally small, this improvement is valuable.

These results described above are obtained across known production methods for the carbon black. Tests have been conducted on a wide variety of carbon black materials produced from Super Abrasion Furnace, Intermediate Abrasion Furnace, High Abrasion Furnace, as well as carbon black produced in the environmentally motivated modified tire pyrolis methods.

The addition of the alumina/SiC whisker compositions to carbon black does not negatively impact the advantages of the carbon black over other materials with respect to chemiabsorbed volatile content. The whisker sizes must be matched to the sizes of the carbon black particles, since that carbon black sizing is critical for the most efficient and most effective blending with the rubber and the best reinforcement. Very small particle sizes result in high reinforcement but are difficult to distribute within the rubber, while large sizes are more easily distributed but provide less reinforcing.

D. Providing Advantages in Other Implementations.

The disclosed SiC/Al$_2$O$_3$ composites produced as described above exhibit increased thermal stability and shock resistance when compared with raw SiC. In addition the disclosed compositions have undiminished dimensional, electrical conductivity, resistivity, dielectric properties, compressive strength, and density characteristics when compared with raw SiC. Thus, the disclosed materials may be advantageously used in the formation many products, materials, or devices currently fabricated with alumina or SiC. Several implementations are discussed in detail below.

The disclosed SiC/Al$_2$O$_3$ composites may be used in the fabrication of high temperature and high power electronics and assemblies of such devices, including but not limited to 11-25 kV high voltage, low capacitance transformer test beds or zirconium-diboride devices.

It is generally desired that high power electronics be as small as possible while maintaining both the electrical and mechanical characteristics required. When implemented in an electronic device, the disclosed compositions add strength without greatly increasing weight since the resulting material can be thinner and smaller. 2008 data from the Center for Composite Materials, Harbin Institute of Technology, Harbin, PRC, (Xinghong Zhang, Lin Xu, Wenbo Han, Ling Weng, Jiecai Han and Shanyi Du: *Microstructure and properties of silicon carbide whisker reinforced zirconium diboride ultra-high temperature ceramic*), which shows that SiC (up to 30% by volume) added to monolithic ZrB2 showed: "Flexural strength increased from 629 MPa for pure ZrB2 to 767 MPa [for ZrB2-30 vol % SiCw]. Likewise, fracture toughness ranged from 5.4 to 7.1 MPa m1/2 over the same composition range. Specific heat capacity increased with SiC whisker addition, while thermal diffusivity and thermal conductivity decreased slightly with the increase of SiC whisker content."

The disclosed materials may be advantageously used in a number of microwave and waveguide applications as well as in lower ceramics technology applications requiring high resistivity and dielectric strength, such as high tension insulators and spark plugs.

The disclosed SiC/Al$_2$O$_3$ composites have suitable size and morphology for admixing with untreated alumina (Al$_2$O$_3$) when employed as a oxide mixer for use in atmospheric plasma flame reduction process as well as PVD, CVD, and Low Pressure Vacuum Plasma Spraying. This application of the disclosed materials shows good potential for lowering the "contact time" of the plasmas used to coat a work in progress, although the precise mechanism by which this happens is still being researched and is not completely understood. It is presently known that the thermal distribution properties are more regular and more consistent with regard to piece to piece replicability, while the coating time is reduced by 25-28%. The reduction in coating time can lead to significant improvement in the number of items which can be coated in any work shift, which leads to higher machine utilization and lower production costs.

The disclosed SiC/Al$_2$O$_3$ composites also exhibit the necessary characteristics and suitable size and morphology for admixing with untreated SiC used as a carbide base for use in an atmospheric plasma flame reduction process as well as PVD, CVD, and Low Pressure Vacuum Plasma Spraying.

The disclosed SiC/Al$_2$O$_3$ composites exhibit the necessary characteristics and are suitable in size for admixing with Al$_2$O$_3$ or Al$_2$O$_3$ composites used in specialty bearings or in medical implants or similar devices as a composite structural element. For example, greater strength with lighter weight is of importance in aerospace and aviation applications. The increased structural strength exhibited by a ceramic material enhanced with the disclosed compositions is approximately 1.85-2 times that of unenhanced Al$_2$O$_3$ or Al$_2$O$_3$ composites.

The disclosed SiC/Al$_2$O$_3$ composites exhibit the necessary characteristics and are suitable in size for admixing with Al$_2$O$_3$ or Al$_2$O$_3$ composites used used in poly-coating materials (such as polyurethane barrier coatings). Baseline laboratory tests (for example, durometer and Taber abrasion tests) demonstrate that the resulting coating has significantly greater life than a coating not including the disclosed SiC/Al$_2$O$_3$ composites. For example, a 10-fold improvement in the strength and longevity of wood floor poly coatings has been demonstrated by adding a 5% by weight loading of an Al$_2$O$_3$, Al$_2$O$_3$ composite versus simple addition of Al$_2$O$_3$ to the floor coating material.

The described SiC/Al$_2$O$_3$ compositions are suitable in size and character for admixing with various rubber compositions and rubber composites, for example, the described SiC/Al$_2$O$_3$ compositions may be mixed with Hydrogenated Nitrile Butadiene Rubber (HNBR) used in high temperature seals such as Blow Out Prevention Seals, and high velocity rotating and reciprocating seals used in aircraft and high performance engines.

HNBR blow out prevention (BOP) seals treated with SiC have been repeatedly shown to provide three (3) or more times the life of untreated BOP Seals. For example, one series of tests showed that rather than a normal wear-out point of 100,000 feet of pushed and pulled well pipe through the BOP seal, a seal treated with SiC lasted for over 295,000 feet, a 2.9:1 improvement. This data is consistent with known findings that treated HNBR surfaces have a 3× improvement in overall friction based wear resistance; 70% less wear in rotating shaft seals; and 70% reduction in stick-slip test times.

It is anticipated that adding about 1.5% or less by volume of the disclosed SiC/Al$_2$O$_3$ compositions will result in significant improvements in the operating life of flexible Thermoplastic Urethane (TPU) units, such as flex hose with a greater than 3.5% improvement in the number of flex cycles before failure expected. Similarly, the disclosed SiC/Al$_2$O$_3$ compositions may be admixed into the TPU coating of TPU coated parts, resulting in significant performance improvement, especially with respect to material loss during operation. For example, it has been shown that at 5% SiC loading the material loss was reduced to half and with 10% loading a further reduction of 12-15% depending on application.

Similarly, the SiC/Al$_2$O$_3$ compositions may be admixed with cast polyurethane (C-PU), for example in hydrocyclone inserts, and will serve to reduce material loss during hydrocyclone operation by half. In particular, the material loss at 1030 starts with untreated C-PU averaged <0.0259% while losses with treated material was determined to be 0.094-0.095%.

The inclusion of the disclosed SiC/Al$_2$O$_3$ compositions in both epoxy and vinyl ester gel coatings also resulted in reductions in material weight loss during operation. In this implementation, a reduced material weight loss of up to 42% in epoxy coated parts was observed. Other uses where the disclosed SiC/Al$_2$O$_3$ compositions are mixed with a matrix or material to enhance material strength, durability, friction characteristics, thermal characteristics or other characteristics of any type are within the scope of the present disclosure.

As noted in Section I above, the ratios of constituent components in the disclosed compositions may be varied to achieve selected performance characteristics without changing the basic nature of the composition. In particular the ratio of alumina to SiC may be varied to achieve desirable performance characteristics as described above. Certain SiC to alumina ratios that have been investigated for specific uses are tabulated in Table 1 below. Variations from the disclosed ratios may prove equally effective for the noted and other uses.

TABLE 1

| Application | Primary Unit | Approximate SiC:Al$_2$O$_3$ Ratio |
|---|---|---|
| Deep Subsea Syntactic Foams | SiC | 6:1 (6 parts SiC) |
| Lighter Weight Armor | SiC & Alumina | Equal Parts |
| High Temperature/High Power Electronics | SiC & Alumina | Equal Parts |
| Microwave and Waveguides | SiC & Alumina | Equal Parts |
| Insulators and Spark Plugs | SiC | 4:1 (4 parts SiC) |
| Atmospheric Plasma Flame Reduction | Either | Equal or Either |
| Specialty Bearings | SiC | 5:1 (5 parts SiC) |
| Medical Implants | SiC & Alumina | Equal Parts |
| Additive in Poly-coatings | Alumina | 1:8 (8 parts alumina) |
| Additive in High Value Seals | SiC | 8:1 (8 parts SiC) |
| Additive in Thermoplastic Urethanes and Cast Polyurethanes | Alumina | 1:8 (8 parts alumina) |
| Additive in Vinyl and Gel Ester Coatings | SiC OR Alumina | Depends on coloration desired |
| Additive in Carbon Black | SiC | 9.5:1 (9.5 SiC) |

Various embodiments of the disclosure could also include permutations of the various elements recited in the claims as if each dependent claim was a multiple dependent claim incorporating the limitations of each of the preceding dependent claims as well as the independent claims. Such permutations are expressly within the scope of this disclosure. While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims. All references cited herein are incorporated in their entirety by reference.

The description of the embodiments has been presented for purposes of illustration and description, but is not intended to be exhaustive or limiting. The scope of the disclosure is limited only by the scope of the following claims. Many modifications and variations will be apparent to those of ordinary skill in the art. The embodiments described and shown in the figure was chosen and described in order to best explain the principles of the various embodiments, the practical application, and to enable others of ordinary skill in the art to understand the various embodiments while recognizing that various modifications may be made such as are suited to the particular use contemplated.

What is claimed is:

1. A mini-whisker composition comprising:
   0.01 to 35% by weight of Al$_2$O$_3$ orthorhombic whiskers having a length of 10-20 μm and a surface altered by wet etching with hydrofluoric acid;
   0.01 to 98% by weight of SiC orthorhombic whiskers having a length of 10-20 μm and a surface altered by dry etching in a fluorination material; and
   0.01 to 15% by weight of kaolin, altered by treatment with Na$_2$SiF$_6$, the above constituents being blended into a SiC/Al$_2$O$_3$ composite, wherein the etched AL$_2$O$_3$ orthorhombic whiskers and the etched SiC orthorhombic whiskers are physically separate constituents of the composition.

2. The composition of claim 1, wherein the kaolin comprises 99.99% pure kaolin.

3. The composition of claim 1 wherein the fluorination material comprises tetrafluorethylene or polytetrafluoroethylene.

4. The composition of claim 1 wherein the SiC orthorhombic whiskers comprises β SiC and the Al$_2$O$_3$ comprises β Al$_2$O$_3$.

5. A method of producing a mini-whisker composition comprising:
   wet etching Al$_2$O$_3$ orthorhombic whiskers in hydrofluoric acid to produce angularly etched orthorhombic whiskers having a length of 10-20 μm and a surface altered by the wet etching;
   blending dry kaolin with Na$_2$SiF$_6$;
   providing a direct fluorination material;
   providing SiC orthorhombic whiskers, having a length of 10-20 μm; and
   blending 0.01 to 35% by weight of the etched orthorhombic Al$_2$O$_3$ whiskers into 0.01 to 98% by weight of the SiC orthorhombic whiskers, the fluorination material and the kaolin blended with Na$_2$SiF$_6$,
   dry etching the SiC orthorhombic whiskers by heating the blend of orthorhombic etched whiskers of Al$_2$O$_3$, SiC orthorhombic whiskers, kaolin blended with Na$_2$SiF$_6$ and the fluorination material to produce a mixture of the orthorhombic dry etched whiskers of SiC and physically separate etched orthorhombic Al$_2$O$_3$ whiskers.

6. The method of claim 5 wherein the fluorination material comprises tetrafluoroethylene or polytetrafluoroethylene.

7. The method of claim 5 further comprising using a high speed gas dryer to remove up to 99% of water from the blended mixture.

8. The method of claim 5 further comprising processing the blended mixture at a temperature range of 800-810° C.

9. The method of claim 8 further comprising heating the blended mixture in a device selected from; a fluid bed dryer, conveyor oven, rotary kiln, calciner or ceramics furnace.

10. A product formed by a process comprising:
    providing Al$_2$O$_3$ orthorhombic whiskers having a length of 10-20 μm and a surface altered by the wet etching with hydrofluoric acid;
    providing dry kaolin blended with Na$_2$SiF$_6$;
    providing SiC orthorhombic whiskers, having a length of 10-20 μm; and
    blending 0.01 to 35% by weight of the etched orthorhombic Al$_2$O$_3$ whiskers into 0.01 to 98% by weight of the SiC orthorhombic whiskers, the fluorination material and the kaolin blended with NA$_2$SiF$_6$,
    dry etching the SiC orthorhombic whiskers by heating the blend of heating the blend orthorhombic etched whiskers of Al$_2$O$_3$, SiC orthorhombic whiskers, kaolin blended with Na$_2$SiF$_6$ and the fluorination material to form a composition comprising a mixture of the dry etched orthorhombic whiskers of SiC and physically separate etched orthorhombic Al$_2$O$_3$ whiskers; and
    adding the composition to another material to form the product.

11. The product of claim 10 wherein the product is a syntactic foam.

12. The product of claim 11 formed by a process further comprising the steps of:
    mixing the composition at a ratio of about 7.5% to 15% by weight with a quantity of microspheres; and
    mixing the composition and microsphere mixture with a syntactic foam base resin.

13. The product of claim 11 wherein the product is syntactic foam used in armor.

14. The product of claim 11 wherein the product is syntactic foam used as to coat a metallic object.

15. The product of claim 10 wherein the product is an electronic or electromechanical device.

16. The product of claim 10 wherein the product is a coating.

17. The product of claim 10 wherein the product is a ceramic composite product.

18. The product of claim 10 wherein the product is a composite bearing.

19. The product of claim 10 wherein the product is a mechanical device.

20. The product of claim 10 wherein the product is a medical device.

21. The product of claim 10 wherein the product is an additive to at least one of HNBR rubber, cast polyurethane, a vinyl ester coating and a thermoplastic urethane.

* * * * *